United States Patent
Neef et al.

(10) Patent No.: US 9,880,079 B2
(45) Date of Patent: Jan. 30, 2018

(54) METHOD IN THE PREPARATION OF SAMPLES FOR MICROSCOPIC EXAMINATION AND FOR CHECKING COVERSLIPPING QUALITY

(71) Applicant: Leica Biosystems Nussloch GmbH, Nussloch (DE)

(72) Inventors: Bernhard Neef, Nussloch (DE); Christian Wilke, Rimbach (DE); Karl-Heinrich Westerhoff, Eppingen (DE)

(73) Assignee: Leica Biosystems Nussloch GmbH, Nussloch (DE)

(*) Notice: Subject to any disclaimer, the term of this patent is extended or adjusted under 35 U.S.C. 154(b) by 314 days.

(21) Appl. No.: 13/769,859

(22) Filed: Feb. 19, 2013

(65) Prior Publication Data
US 2013/0217065 A1    Aug. 22, 2013

(30) Foreign Application Priority Data

Feb. 21, 2012  (DE) .................. 10 2012 101 377

(51) Int. Cl.
*G01N 1/36* (2006.01)
*G02B 21/34* (2006.01)
(Continued)

(52) U.S. Cl.
CPC ............ *G01N 1/36* (2013.01); *G01N 1/2813* (2013.01); *G01N 1/312* (2013.01); *G02B 21/34* (2013.01); *G06K 9/00127* (2013.01); *G06K 9/036* (2013.01); *G06T 7/0012* (2013.01); *G06T 7/0014* (2013.01); *G02B 21/10* (2013.01); *G02B 21/365* (2013.01); *G06T 2207/10056* (2013.01);
(Continued)

(58) Field of Classification Search
CPC ........ G01N 1/28; G01N 1/2806; G01N 1/312; G02B 21/34
See application file for complete search history.

(56) References Cited

U.S. PATENT DOCUMENTS 5,566,249 A    10/1996    Rosenlof et al.
5,812,692 A    9/1998    Rosenlof et al.
(Continued)

FOREIGN PATENT DOCUMENTS

CN    1337030    2/2002
CN    201611408    10/2010
(Continued)

OTHER PUBLICATIONS

Darnton, B. "The Repair of Broken Coverslips on Paper Covered Slides," accessed on the internet at <URL=http://www.microscopy-uk.org.uk/mag/artmar00/bdcslip.html>, published in the Mar. 2000 edition of Micscape Magazine.*

*Primary Examiner* — Yelena G Gakh
*Assistant Examiner* — Michelle Adams
(74) *Attorney, Agent, or Firm* — Hodgson Russ LLP

(57) ABSTRACT

The invention relates to a method in the preparation of samples for microscopic examination onto which a coverslip is applied. The method is notable for the fact that the coverslipping quality is checked automatically and at least partly optically. The invention further relates to an apparatus for carrying out the method, and to an apparatus for checking the coverslipping quality of samples onto which a coverslip is applied.

20 Claims, 4 Drawing Sheets

(51) Int. Cl.
*G06T 7/00* (2017.01)
*G01N 1/28* (2006.01)
*G01N 1/31* (2006.01)
*G06K 9/00* (2006.01)
*G06K 9/03* (2006.01)
G02B 21/10 (2006.01)
G02B 21/36 (2006.01)

(52) U.S. Cl.
CPC ............... *G06T 2207/10152* (2013.01); *G06T 2207/30024* (2013.01)

(56) References Cited

U.S. PATENT DOCUMENTS

| | | | | |
|---|---|---|---|---|
| 5,835,620 | A | * | 11/1998 | Kaplan ............... G06K 9/00127 356/629 |
| 6,385,403 | B1 | * | 5/2002 | Kojima et al. ................. 396/233 |
| 8,064,678 | B2 | | 11/2011 | Gregson |
| 2003/0047863 | A1 | * | 3/2003 | Lang .................... G01N 1/2813 271/103 |
| 2007/0206097 | A1 | * | 9/2007 | Uchiyama et al. ...... 348/207.99 |
| 2012/0002034 | A1 | * | 1/2012 | Matsunobu et al. ............ 348/79 |
| 2012/0140055 | A1 | * | 6/2012 | Narusawa ............... G02B 21/10 348/79 |

FOREIGN PATENT DOCUMENTS

| | | |
|---|---|---|
| DE | 3432002 | 11/1987 |
| DE | 10144048 | 3/2003 |
| EP | 2402813 A2 | 1/2012 |
| EP | 2461199 A1 | 6/2012 |
| JP | S59157534 | 9/1984 |
| JP | 2006023496 | 1/2006 |
| JP | 2008541179 | 11/2008 |
| JP | 2008301332 | 12/2008 |
| WO | 9722946 A1 | 6/1997 |
| WO | 1998043123 | 10/1998 |
| WO | 2006080239 | 8/2006 |
| WO | WO 2009/086487 A2 * | 7/2009 |

* cited by examiner

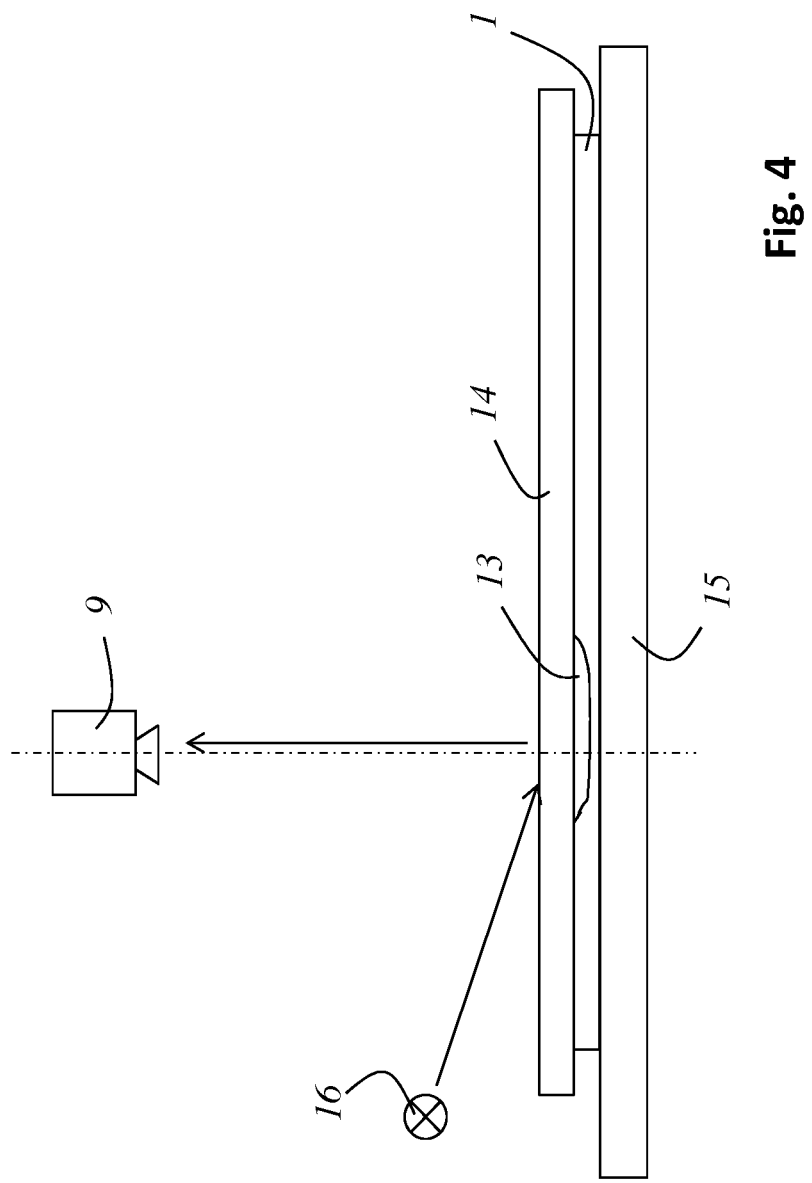

METHOD IN THE PREPARATION OF SAMPLES FOR MICROSCOPIC EXAMINATION AND FOR CHECKING COVERSLIPPING QUALITY

CROSS REFERENCE TO RELATED APPLICATIONS

This application claims priority of German patent application number 10 2012 101 377.2 filed Feb. 21, 2012, the entire disclosure of which is incorporated by reference herein.

FIELD OF THE INVENTION

The invention relates to a method in the preparation of samples for microscopic examination onto which a coverslip is applied. The invention further relates to an apparatus for checking the coverslipping quality of samples onto which a coverslip is applied.

BACKGROUND OF THE INVENTION

In preparation for microscopic investigations, the samples to be investigated, which can e.g. involve a histological section, are usually placed onto a specimen slide and treated with a coverslipping medium, which preferably has a refractive index adapted to the refractive index of the coverslip or of the specimen slide and functions as an adhesive, before a coverslip is then applied. Because coverslipping of the sample is usually a very time-consuming procedure, coverslipping machines are often used for this.

An apparatus for handling specimen slides and coverslips is known, for example, from DE 101 44 048 A1. With this apparatus, a coverslip is respectively received with the aid of a receiving unit guided via an actuation arm, and set onto a desired position on the specimen slide.

A variety of defects can occur in the process of coverslipping. For example, it may happen that the coverslip completely or partly fractures, which can result in the emergence of coverslipping medium as a further defect. As a further defect, air inclusions beneath the coverslip can occur; these can have a disadvantageous influence on a later microscopic investigation, or make it in fact impossible.

When defects occur in the coverslipping process, they are often noticed only upon microscopic examination. This leads to a number of serious problems for routine laboratory operation, since at this point it time it is often not possible to re-coverslip the sample. Especially when a plurality of samples are to be investigated, for example in a continuous throughput, such defects result in a considerable diminution in the overall investigation efficiency of the laboratory, since the entire process sequence, and not just the coverslipping process, becomes disrupted.

U.S. Pat. No. 5,566,249 discloses an apparatus for detecting air bubbles in the coverslipping medium. The apparatus comprises image-generating means with which an image of the coverslip can be generated, and which can be embodied as an automated scanning microscope. Means for recognizing bubble edges, and for further image processing, are also provided.

SUMMARY OF THE INVENTION

The object of the present invention is to describe method which makes it possible to avoid or at least mitigate the problems recited above.

The object is achieved by a method which is characterized in that coverslipping quality is checked automatically and optically at least partly with dark field illumination.

The further object of the present invention is to describe an apparatus that enables rapid and reliable checking of coverslipping quality in samples onto which a coverslip is applied.

The further object is achieved by an apparatus that is characterized by an optical imaging apparatus operating automatically and at least partly with dark field illumination.

It has been recognized in accordance with the present invention that a plurality of problems that can occur during routine laboratory operation as a result of defectively coverslipped samples can be at least mitigated by early and reliable checking of coverslipping quality. An early check as to whether a sample is defectively coverslipped, and preferably an identification as to the nature of an identified defect, make it possible to keep the subsequent laboratory processes, in particular microscopic examination, largely free of defectively coverslipped samples. The possibility is also created of contemporaneously eliminating coverslipping defects that are identified, for example by re-coverslipping.

In a particular embodiment of the invention, a check is made as to whether the coverslip is damaged after a coverslipping operation, in particular as to whether the coverslip exhibits a fracture after a coverslipping operation. Alternatively or additionally, provision can be made that a check is made as to whether air inclusions are present in a coverslipping medium and/or as to whether air inclusions are present between the coverslip and the sample. Provision can furthermore be made, alternatively or additionally, that a check is made as to whether surface irregularities of the coverslip are present.

In order to carry out the checks recited above, advantageously at least one, preferably microscopic, image of the coverslip and/or of the coverslipping medium can be generated. Provision can be made in particular that a grayscale image is generated as an image. The generation of an image of the coverslip and/or of the embedding medium makes possible, especially if digital image data are generated, an automatic, for example computer-controlled evaluation with regard to the presence and/or nature of coverslipping defects. Provision can in particular be made here that image patterns of known coverslipping defects and/or of particularly frequently occurring coverslipping defects are stored in a memory, and are compared with image details of the generated image.

The coverslip and/or the embedding medium is suitably illuminated in order to generate the image, in which context provision can be made in particular that the image is generated with bright field illumination. It has been found that it is particularly advantageous firstly to generate a first image under bright field illumination in order to classify the imaged objects and optionally compare them with reference patterns.

Acquisition of an image occurs preferably in the context of an axially symmetrical arrangement of the (incident) bright field illumination system and camera with respect to the specimen slide, the result being that a largely parallel wavefront strikes the entire surface of the coverslip, and reflects well and is therefore also easily detectable. The object located beneath the coverslip remits the light, and a portion of that light also travels to the detector.

Coverslipping defects, such as air inclusions, surface irregularities, or glass fracture, result in reflections of the illumination light that substantially differ from the reflections that occur in the context of a sample coverslipped without defects. This becomes particularly clearly apparent in a grayscale image. In this, air inclusions result in increased reflection and appear in the image as bright regions. Surface irregularities and fractures in the coverslip deflect the light and appear in the image as particularly dark regions, since less light travels from these regions to the detector.

A determination is preferably made, by calibration, of the optimum exposure time allowing the background to be imaged in the neutral-gray region, so that particularly bright and/or particularly dark regions stand out particularly well from the background.

When the sample is illuminated with a directional illumination, in addition to reflection of the illumination light at the air-glass interfacial layer a reflection also occurs at the interface between an enclosed air bubble and the coverslipping medium (adhesive) surrounding it. A double reflection therefore occurs in the case of an air bubble, so that air bubbles appear in the image as very particularly bright regions. It is preferred to use those materials and angles of incidence which ensure that the reflectance of the background exceeds a specific value, so that the reflection of the air inclusions is always greater than the reflections at other components, for example at interfaces of the specimen slide or of the coverslip. To ensure this, for example, specimen slides or coverslips having particular optical coatings can be used.

By preference, all the parameters are selected so that the background appears with a grayscale value of 100, while air inclusions exhibit in the image a grayscale value of approximately 200. It has been found that the detection of air inclusions functions reliably if they exhibit a contrast of at least 20% with the background.

A deviation of the surface geometry of the coverslip from an ideal planar surface causes incident light to be reflected with a double angular error. In addition, the light reflected from the coverslip no longer exhibits a completely flat wavefront. The detection geometry is preferably selected in such a way that the light reflected from the fault does not travel to the detector. The image of the fault thus appears darker than the background. The detection distance, the size of an entrance opening of the detector, and the aperture of the detector (for example, camera) are, in particular, to be selected accordingly.

In a particularly advantageous embodiment, contours of the regions that exhibit a contrast of more than 20% with the background are calculated, for example by an evaluation apparatus. The regions identified can then be filtered in terms of grayscale values, and associated with coverslipping defects.

Alternatively or in addition to the generation of an image with bright field illumination, provision can also be made that an image with dark field illumination is generated. A very particularly precise and reliable embodiment is one in which firstly a first image is generated in bright-field in order to classify the imaged objects, and then a second image is generated with a dark field illumination in order to achieve a more precise classification of the objects found in the context of bright field illumination.

A dark field illumination is notable in particular for the fact that the illumination light is incident onto the object with sufficient obliquity that the reflected illumination rays are not incident into the objective and thus do not contribute to image creation. The result achieved thereby is, in particular, that exclusively refracted or scattered light contributes to image creation. Advantageously, the object structures then usually appear as bright on a dark background.

Dark field illumination is achievable, for example, by illuminating at a flat angle (large angle of incidence of the illumination light relative to the surface normal of the coverslip). Bright, sharply delimited objects then appear in the image, with high contrast with respect to the background. Provision can be made in this context that the illumination exhibits a semicircular pattern, so that the detected object contours are thus not complete and continuous.

For accurate classification of the half-discovered image objects, an additional check can be made in the image generated with dark field illumination as to whether artifacts (e.g. particular reflections) occur at the same location in the image. It is thereby possible to distinguish particularly reliably whether artifacts detectable in one of the images are to associated with a coverslipping defect or are, for example, caused by the specimen itself.

As already mentioned, provision can advantageously be made that the image or images is or are automatically evaluated by an evaluation apparatus, and/or that the image or images is or are automatically evaluated by an evaluation apparatus comprising a data processing device, in particular a PC. An embodiment of this kind is not only particularly fast, but moreover also particularly reliable and precise.

As already explained, an embodiment in which both an image with bright field illumination and an image with dark field illumination are generated, and in which the images are then compared with one another (for example by an evaluation apparatus), gives information in particularly reliable fashion as to whether a coverslipping defect is present, and which coverslipping defect is involved. This is particularly reliable when a check is made (for example, by an evaluation apparatus) as to whether, for a detected detail of the one image, a correspondence is present in the other image.

In a particular embodiment, provision is made that the image acquisition angle and/or the illumination angle is individually adjusted in a manner adapted to the nature and size of the sample to be investigated. It can be advantageous in this context to use an apparatus which allows the image acquisition angle and/or the illumination angle to be (preferably steplessly) adjusted.

An apparatus of this kind furthermore has the advantage that it can be used both to generate an image with bright field illumination (for example with a 0° angle of incidence of the illumination light) and to generate an image with dark field illumination (for example with an angle of incidence for the illumination light in the range from 50 to 80°). In particular, with an apparatus of this kind the sample can remain on the sample stage and/or in a sample mount after a bright field image is generated, and dark field illumination can be generated immediately after modifying the image acquisition angle and/or the illumination angle. Provision can be made in particular that the illumination light source and/or the detector (for example, camera) are each mounted on pivotable stand arms. Alternatively or additionally, it is also possible to pivot the respective beam paths, for example with the aid of rotatable mirrors.

Particularly reliable results are achieved if the average brightness and/or the brightness distribution of a reference image, in particular of a coverslipped specimen slide without a sample, is measured—manually or automatically—before the coverslipping quality is checked. The grayscale value distribution of the reference measurement is preferably stored so that it can be compared with the grayscale value distribution of subsequent images in the context of the investigation of coverslipped samples. In particular, a shading correction can be carried out (for example, by an evaluation apparatus) for each image with the aid of the reference measurement, in particular on the basis of the measured brightness and/or brightness distribution. Because ambient conditions can change over time, provision can advantageously be made that the calibration operation is repeated at predefined or acceptable time intervals. Relevant changes in ambient conditions can be, for example, the ambient temperature or the modified radiating behavior of an aging illumination light source.

In particular, provision can advantageously be made that from the measured average brightness and/or brightness distribution, an exposure time for generating an image is calculated, and/or that from the measured average brightness and/or brightness distribution, an exposure time for generating an image is calculated in such a way that a predetermined or predeterminable brightness for the background is achieved.

In a particular embodiment, provision is made that firstly an overview image is generated and/or that a sample-specific code, in particular a barcode attached to a specimen slide or to a coverslip, is read out. Provision can be made in particular that the overview image is generated with an imaging apparatus for checking coverslipping quality, and/or that a sample-specific code, in particular a barcode attached to a specimen slide or to a coverslip, is read out with an imaging apparatus for checking coverslipping quality.

An embodiment of this kind has the advantage that the sample to be investigated can be identified and, for example, associated with a patient, on the basis of features that have nothing to do with the detection of coverslipping defects. Provision can moreover be made that in addition to a check for coverslipping defects, the staining quality, in particular the staining quality of a hematoxylin-eosin stain, and/or a color intensity, can be checked. The same apparatus that is also used to check coverslipping quality can be used in this context. This has the particular advantage that an additional apparatus is unnecessary, and that the sample does not need to be transferred into a further apparatus; the ultimate result is that time can be saved.

As already explained with reference to examples, provision can be made that the same coverslipping result is checked in chronologically sequential fashion under different conditions, and/or that the same coverslipping result is checked in chronologically sequential fashion under different conditions at different testing stations.

As already mentioned, an imaging apparatus, in particular an imaging apparatus having dark field illumination, can be used particularly advantageously to check the coverslipping quality of samples onto which a coverslip is applied.

In a particular embodiment of an apparatus according to the present invention for checking the coverslipping quality of samples, which comprises an automatically operating optical imaging apparatus, a evaluation apparatus, preferably operating automatically, that investigates at least one image generated by the imaging apparatus is additionally provided. Provision can be made in particular that an evaluation apparatus of this kind investigates an image generated by the imaging apparatus as to whether the coverslip is damaged after a coverslipping operation and/or whether the coverslip exhibits a fracture after a coverslipping operation and/or whether air inclusions are present in a coverslipping medium and/or whether air inclusions are present between the coverslip and the sample and/or whether surface irregularities of the coverslip are present.

For this purpose in particular, provision can be made that the imaging apparatus generates at least one image of the coverslip and/or of the coverslipping medium, and/or that the imaging apparatus generates at least one microscopic image of the coverslip and/or of the coverslipping medium, and/or that the imaging apparatus generates a grayscale image.

An advantageous embodiment of an apparatus according to the present invention contains an illumination apparatus for illuminating the coverslip and/or the embedding medium upon generation of an image, in which context the illumination apparatus can be designed to generate a bright field illumination and/or a dark field illumination. As already mentioned, provision can advantageously be made here that both a bright field illumination and a dark field illumination is generated with one and the same illumination apparatus.

Provision can be made in particular that the evaluation apparatus calculates, from a measured average brightness and/or brightness distribution of a reference image, in particular of a coverslipped specimen slide without a sample, an exposure time for generating an image, and/or that the evaluation apparatus calculates, from a measured average brightness and/or brightness distribution of a reference image, in particular of a coverslipped specimen slide without a sample, an exposure time for generating an image in such a way that a predetermined or predeterminable brightness for the background is achieved upon generation of the image.

As already mentioned, provision can advantageously be made that the apparatus is embodied to generate an overview image and/or to read out a sample-specific code, in particular a barcode attached to a specimen slide or to a coverslip. In particular, the apparatus can advantageously be embodied to check the same coverslipping result in chronologically successive fashion under different conditions and/or at the different testing stations.

In a particular embodiment of the apparatus according to the present invention that exhibits a particularly high level of automation, a handling apparatus that conveys a coverslipped sample to be investigated into a scanning region of the imaging apparatus is provided. Provision can be made here in particular that the handling apparatus operates automatically.

A handling apparatus of this kind can, for example, sequentially remove coverslipped samples to be investigated from a receiving apparatus, in particular from a stacking shelf, and transfer them into a scanning region of the imaging apparatus. Provision can furthermore be made that the handling apparatus deposits each sample back into the receiving apparatus after it has been checked.

An apparatus for checking coverslipping quality can be part of a coverslipping machine and/or can be integrated into a coverslipping machine. Both coverslipping and checking of coverslipping quality can thus occur in a single arrangement. Provision can furthermore be made that the coverslipping operation is repeated, in particular automatically, if a coverslipping defect has been identified.

Alternatively to integration of the apparatus for checking coverslipping quality into a coverslipping machine, provision can also be made that the apparatus for checking coverslipping quality is embodied to, in particular automatically, receive at least one sample equipped with a coverslip from a coverslipping machine, or to remove it from a coverslipping machine.

To allow even a larger number of samples to be reliably analyzed and processed in a short time, provision can advantageously be made that data regarding coverslipping quality, and/or a sample-specific code, in particular a barcode attached to a specimen slide or to a coverslip, are transferred to a higher-level data processing system. Alternatively or additionally, provision can be made that data, for example data regarding coverslipping quality, and/or a sample-specific code, in particular a barcode attached to a specimen slide or to a coverslip, and/or data regarding patient data to be associated with the sample and/or regarding the current whereabouts of the sample, are exchanged with a higher-level data processing system.

According to a particular inventive concept, particularly reliable processing and investigation, in particular even of larger quantities of samples, is possible with a sample processing system that is equipped with an apparatus according to the present invention. This can comprise, in particular, a higher-level data processing system that receives data regarding coverslipping quality, and/or a sample-specific code, in particular a barcode attached to a specimen slide or to a coverslip, and/or data regarding patient data to be associated with the sample and/or regarding the current whereabouts of the sample, from the apparatus for checking coverslipping quality. The higher-level data processing system can comprise, in particular, a memory for storing these data. Provision can also be made that the received data are compared with previously stored data, for example in order to control further processing of the sample. Provision can also be made that the sample processing system comprises a higher-level data processing system with which the apparatus for checking coverslipping quality exchanges data, for example data regarding coverslipping quality or the whereabouts of the sample, or regarding patient data to be associated with the sample.

Further objectives, advantages, features, and utilization capabilities of the present invention are evident from the description below of an exemplifying embodiment with reference to the drawings. All features described and/or illustratively depicted, of themselves or in any useful combination, constitute the subject matter of the present invention, independently of their grouping in the claims or their internal references.

DETAILED DESCRIPTION OF THE INVENTION

Figure 1:
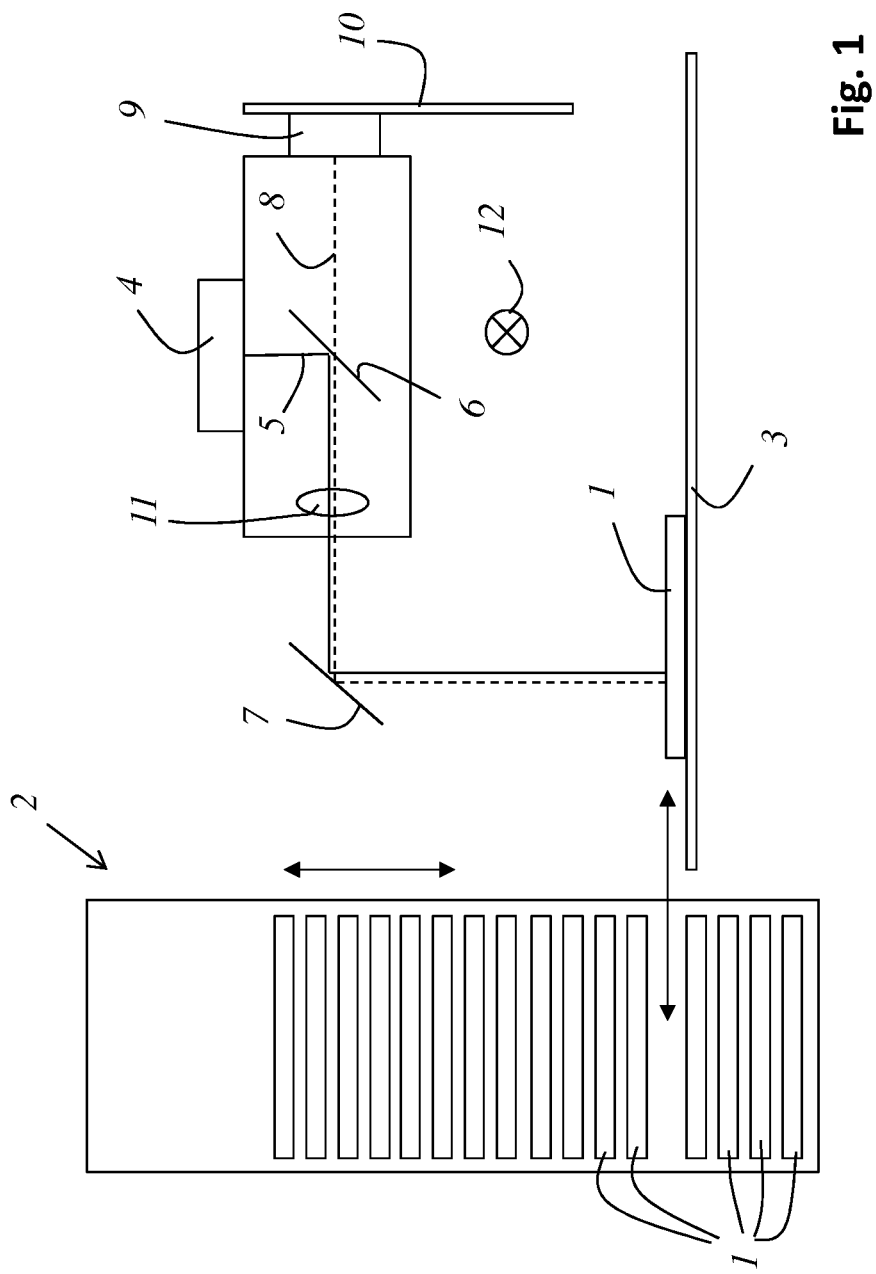
FIG. 1 shows an exemplifying embodiment of an apparatus for checking the coverslipping quality of samples onto which a coverslip is applied, FIG. 2 schematically shows the generation of an image of a coverslipped sample under bright field illumination when an air inclusion is present, FIG. 3 schematically shows the generation of an image of a coverslipped sample under bright field illumination when a fracture of the coverslip is present, and FIG. 4 schematically shows the generation of an image with dark field illumination.

FIG. 1 is a schematic general depiction of an exemplifying embodiment of an apparatus for checking the coverslipping quality of samples 1 onto which a coverslip 16 (not depicted in FIG. 1) is applied. The apparatus comprises a handling apparatus (not depicted in further detail) that removes a respective coverslipped sample 1 to be investigated from a stacking shelf 2 and places it in a scanning region on a sample stage 3. After each sample 1 has been investigated, the handling apparatus places the investigated sample 1 back into stacking shelf 2. These operations are indicated by the horizontal double arrow.

Stacking shelf 2 can be displaced in a vertical direction, so that a further sample 1 to be investigated can be brought to the level of sample stage 3 and then removed. This operation is indicated by the vertical double arrow.

The apparatus for checking coverslipping quality comprises a first light source 4 for bright field illumination. First light source 4 emits a first illumination light bundle 5 that is directed by a beam splitter 6 and by a deflection mirror 7 to the coverslipped sample 1 to be investigated. Detected light 8 (drawn with dashed lines) reflected from the sample travels along the same light path in the opposite direction, i.e. via deflection mirror 7 back to beam splitter 6, passes through the latter, and lastly arrives at detector 9, which is embodied as a CCD camera. Detector 9 is located on an electronic circuit board 10 that carries an evaluation electronics system (not further depicted).

Also provided are optical components, in particular a telecentric optic, for guiding and shaping the illumination light and detected light, said components being indicated merely schematically and in exemplifying fashion as lens 11.

The apparatus furthermore comprises a further light source 12, drawn in merely schematically, for dark field illumination. Further light source 12 can be, in particular, a semi-annular light source.

Provision can be made, for example, that the apparatus for checking coverslipping quality outputs an optical or acoustic signal as soon as a coverslipping defect is discovered.

Figure 2:
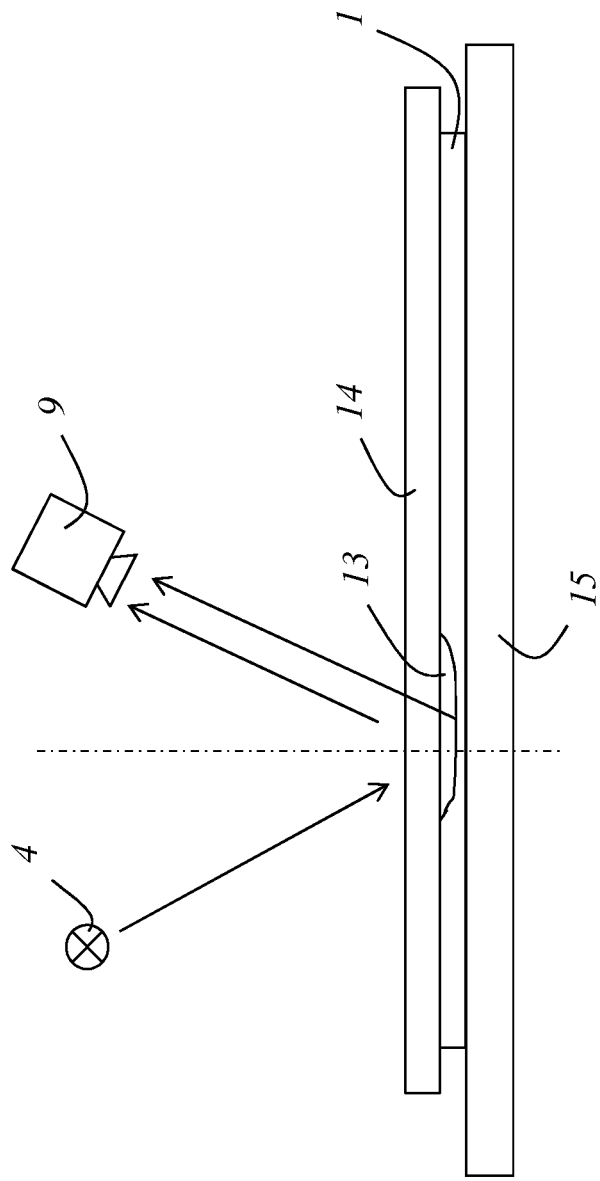

FIG. 2 schematically shows the generation of an image, in particular a grayscale image, under bright field illumination when an air inclusion 13 is present under coverslip 14 of a sample 1 located on a specimen slide 15. A light source 4 that emits light toward the coverslipped sample 1 serves for bright field illumination. The light reflected from the coverslipped sample 1 is detected with a detector 9 that is embodied as a camera.

Additional reflections occur in particular at the transition between air inclusion 13 and the material of sample 1 or its coverslipping medium (adhesive), and cause this region to appear particularly bright in the grayscale image as compared with the background.

Figure 3:
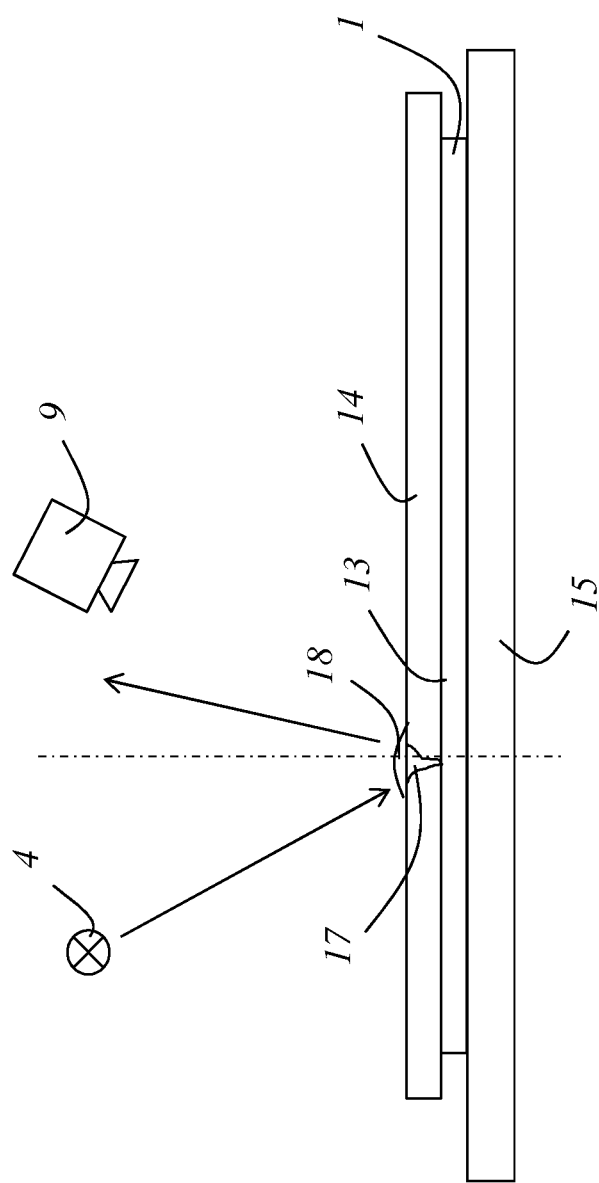

FIG. 3 schematically shows the generation of an image, in particular a grayscale image, of a coverslipped sample 1 under bright field illumination when a fracture 17, filled with coverslipping medium (adhesive), of coverslip 14 is present. Especially because of the irregular surface structure of fracture 17 and of adhesive 18 that has emerged in this region, the light emitted from light source 4 is reflected in a different direction from the light that strikes the coverslipped sample 1 in a region in which a coverslipping defect is not present.

The distances, angles, and optical properties are selected in such a way that none of the light reflected in the region of fracture 17, or only a small portion of that light, arrives at detector 9. The consequence of this is that the region of fractured 17 appears particularly dark in the grayscale image relative to the background.

Be it noted that in the context of bright field illumination, the angle of incidence of the illumination light does not necessarily need to be equal to 0°. In particular, angles of incidence in the range from 0° to 30° relative to the incidence perpendicular, i.e. relative to the vertical in terms of the (unconfirmed) coverslip surface, are also used in practice in bright field illumination. The position of the detector in this context should preferably be selected so that no reflected light, but instead exclusively refracted and/or scattered light, arrives at the detector.

FIG. 4 schematically shows the generation of an image, in particular a grayscale image, with dark field illumination. The illumination light of light source 16 is incident relative to sample 1 at a flat angle, i.e. at a large angle of incidence relative to the surface normal of the coverslip. Detection occurs with a vertical view onto sample 1.

The image that is generated shows bright, sharply delimited objects with high contrast, enabling identification of coverslipping defects, in particular automatic identification of coverslipping defects. In particular, an image of this kind generated under dark field illumination makes it possible to check the results of the evaluation of a previously performed investigation with bright field illumination. In particular, it is possible to check whether, for a detected detail of the one image, a correspondence is present in the other image.

The invention is not to be limited to the specific embodiments disclosed, and modifications and other embodiments are intended to be included within the scope of the invention.

PARTS LIST

1 Coverslipped sample
2 Stacking shelf
3 Sample stage
4 First light source for bright field illumination
5 Illumination light bundle
6 Beam splitter
7 Deflection mirror
8 Detected light
9 Detector
10 Electronic circuit board
11 Lens
12 Further light source
13 Air inclusion
14 Coverslip
15 Specimen slide
16 Light source for dark field illumination
17 Fracture of coverslip 14
18 Emerged adhesive

What is claimed is:

1. A method of preparing samples for microscopic examination, comprising:
  automatically and optically checking quality of a solid coverslip on a specimen slide with dark field illumination when the specimen slide is in a coverslipping apparatus, wherein the solid coverslip is a glass coverslip;
  checking a staining quality of a stain applied to the specimen slide using the coverslipping apparatus when the specimen slide is in the coverslipping apparatus;
  automatically identifying, based on the dark field illumination, a defective coverslipped slide using an evaluation apparatus, wherein the defective coverslipped slide exhibits at least one of:
    damage to the solid coverslip;
    fracture in the solid coverslip;
    presence of air inclusions in a coverslipping medium;
    presence of air inclusions between the solid coverslip and a sample on the specimen slide; and
    presence of surface irregularities of the solid coverslip; and
  based on results of the evaluation apparatus, re-coverslipping the defective coverslipped slide or excluding the defective coverslipped slide from at least one microscopic examination and providing a non-defective coverslipped slide to a subsequent laboratory process.

2. The method according to claim 1, further comprising generating an image of at least one of the solid coverslip or the coverslipping medium.

3. The method according to claim 2, wherein the image is a grayscale image.

4. The method according to claim 2, wherein the image comprises a microscopic image.

5. The method according to claim 2, wherein the solid coverslip or the coverslipping medium is illuminated during the generating.

6. The method according to claim 2, wherein the image is automatically evaluated by the evaluation apparatus.

7. The method according to claim 2, wherein the image is acquired at an image acquisition angle or an illumination angle, and wherein the image acquisition angle or the illumination angle is adjustable.

8. The method according to claim 2, further comprising measuring at least one of average brightness or brightness distribution of a reference image of a coverslipped specimen slide without a sample before the checking.

9. The method according to claim 8, wherein an exposure time for the generating is calculated from at least one of the average brightness or the brightness distribution of the reference image.

10. The method according to claim 9, further comprising obtaining a brightness of a background of the image, wherein the air inclusions are present between the solid coverslip and the sample on the specimen slide, and wherein reflection of illumination light by the air inclusions produces corresponding regions in the image having a brightness greater than the brightness of the background of the image.

11. The method according to claim 8, wherein a shading correction of the image is carried out on a basis of at least one of the average brightness or the brightness distribution.

12. The method according to claim 2, further comprising additionally checking the image with regard to at least one of the staining quality of a hematoxylin-eosin stain or a color intensity.

13. The method according to claim 2, further comprising generating an image of at least one of the solid coverslip or a coverslipping medium with bright field illumination.

14. The method according to claim 13, further comprising comparing the image in bright field illumination and an image in dark field illumination with one another.

15. The method according to claim 13, further comprising checking whether correspondence exists between the image with bright field illumination and an image with dark field illumination with respect to a detected detail present in at least one of the image with bright field illumination or the image with dark field illumination.

16. The method according to claim 1, further comprising generating an overview image for the checking of the solid coverslip on the specimen slide.

17. The method according to claim 1, further comprising reading out a barcode attached to the specimen slide.

18. The method according to claim 1, wherein the checking is sequentially performed under two different conditions or at different testing stations.

19. The method according to claim 1, further comprising additionally checking at least one of the staining quality of a hematoxylin-eosin stain or a color intensity.

20. The method according to claim 1, further comprising exchanging data regarding the checking with a higher-level data processing system.

* * * * *